(12) United States Patent
McMillin et al.

(10) Patent No.: US 6,416,467 B1
(45) Date of Patent: Jul. 9, 2002

(54) VAGINAL SPECULUM AND METHOD OF USING SAME

(76) Inventors: Matthew McMillin, 158 E. Fulton, Farmington, IL (US) 61531; James McMillin, 850 N. Dewitt Pl. #13A, Chicago, IL (US) 60611; Jennifer Baumstark, 4714 N. Laurel Dr., Peoria, IL (US) 66614

( * ) Notice: Subject to any disclaimer, the term of this patent is extended or adjusted under 35 U.S.C. 154(b) by 0 days.

(21) Appl. No.: 09/662,572

(22) Filed: Sep. 15, 2000

(51) Int. Cl.$^7$ .................................................. A61B 1/32
(52) U.S. Cl. ........................................ 600/224; 600/220
(58) Field of Search ................................... 600/220, 224, 600/222, 214, 215

(56) References Cited

U.S. PATENT DOCUMENTS

| | | | |
|---|---|---|---|
| 1,157,202 A | * 10/1915 | Bates et al. | 600/215 |
| 3,565,061 A | 2/1971 | Reynolds | |
| 3,575,163 A | 4/1971 | Gasper | |
| 3,744,481 A | 7/1973 | McDonald | |
| 3,747,591 A | 7/1973 | Golden | |
| 3,752,149 A | 8/1973 | Ungar et al. | |
| 3,769,968 A | 11/1973 | Blount et al. | |
| 3,789,829 A | 2/1974 | Hasson | |
| 3,789,835 A | 2/1974 | Whitman | |
| 3,815,585 A | 6/1974 | Fiore | |
| 3,841,318 A | 10/1974 | Olson | |
| 3,851,642 A | 12/1974 | McDonald | |
| 3,890,961 A | 6/1975 | Moore et al. | |
| 3,985,125 A | 10/1976 | Rose | |
| 4,067,323 A | 1/1978 | Troutner et al. | |
| 4,202,324 A | 5/1980 | Alison | |
| 4,210,133 A | 7/1980 | Castaneda | |
| 4,263,898 A | 4/1981 | Wannag | |
| 4,432,351 A | 2/1984 | Hoary | |
| 4,492,220 A | 1/1985 | Hayes | |
| 4,597,383 A | 7/1986 | VanDerBel | |
| 4,766,887 A | 8/1988 | Cecil, Jr. et al. | |
| 4,807,600 A | 2/1989 | Hayes | |
| 4,854,300 A | 8/1989 | Corbo | |
| 4,905,670 A | 3/1990 | Adair | |
| 4,971,036 A | 11/1990 | Collins | |
| 4,994,070 A | 2/1991 | Waters | 606/191 |
| 5,007,409 A | 4/1991 | Pope | |
| 5,052,372 A | 10/1991 | Shapiro | |
| 5,063,908 A | 11/1991 | Collins | |
| 5,072,720 A | 12/1991 | Francis et al. | |
| 5,143,054 A | 9/1992 | Adair | |
| 5,179,937 A | 1/1993 | Lee | |
| 5,231,973 A | 8/1993 | Dickie | |
| 5,243,966 A | 9/1993 | Ng | |
| 5,251,613 A | 10/1993 | Adair | |
| 5,395,354 A | 3/1995 | Vancaillie | 604/317 |
| 5,458,595 A | 10/1995 | Tadir et al. | 606/15 |
| 5,465,709 A | 11/1995 | Dickie et al. | 600/223 |
| 5,499,964 A | 3/1996 | Beck et al. | 600/220 |
| 5,667,481 A | * 9/1997 | Villalta et al. | 600/224 |
| 5,688,223 A | * 11/1997 | Rosendahl | 600/224 |
| 5,865,729 A | 2/1999 | Meehan et al. | 600/207 |
| 5,873,820 A | 2/1999 | Norell | 600/220 |
| 5,997,474 A | 12/1999 | Batchelor | 600/220 |
| 6,004,265 A | 12/1999 | Hsu et al. | 600/223 |
| 6,024,697 A | * 2/2000 | Pisarik | 600/224 |
| 6,074,343 A | * 6/2000 | Nathanson et al. | 600/224 |
| 6,174,282 B1 | * 1/2001 | Tan | 600/224 |

OTHER PUBLICATIONS

The Patton Speculum brochure, date of initial publication unknown.

* cited by examiner

*Primary Examiner*—Paul J. Hirsch
(74) *Attorney, Agent, or Firm*—Barnes & Thornburg

(57) ABSTRACT

A medical instrument for expanding a cavity within a body to perform obstetrical and gynecological examinations and procedures, which includes a handle and pluralities of blades. One plurality of blades includes adjustable longitudinal blades for expanding the vaginal cavity in a vertical direction, and these blades are mounted upon the handle. Another plurality of blades includes adjustable latitudinal blades for expanding the vaginal cavity in a horizontal direction, and these blades are also mounted upon the handle.

19 Claims, 4 Drawing Sheets

VAGINAL SPECULUM AND METHOD OF USING SAME

FIELD OF THE INVENTION

This invention relates to a speculum, a medical device for expanding a cavity within the body of a patient. In particular, the invention related to a vaginal speculum for use during obstetrical/gynecological examination and procedures.

BACKGROUND

Currently available vaginal specula generally include a pair adjustable, longitudinally arranged blades and handles. These bladed are inserted into the vaginal opening and pivotally adjusted to expand the cavity. Specula are typically used by medical practitioners, especially obstetricians, gynecologists, and surgeons, to visually observe the vaginal walls, cervix or uterus, and to create a cavity within the body in which to perform various procedures. Most currently available vaginal specula push the tissue along the vertical axis of the vaginal opening by pivoting at fulcrum located between the blades and the handles.

However, expanding the cavity along a single axis can be an inefficient method for the practitioner. Many patients have extraneous tissue which can intrude around the sides of the speculum blades into the physician's filed of view through the vaginal canal. These patients include those who are multiparous, patients who are currently gaining weight during pregnancy, and those who simply have extraneous tissue or localized flaccid tissue. In some instances, the intruding tissue decreases the size of the cavity created by the speculum. More importantly, the tissue can impede the practitioners view of the vaginal interior, making the examination or procedure more difficult, time consuming and thereby impeding the practitioner's efficiency.

In order to overcome these problems, some practitioners have employed a second instrument to retract the tissue from their field of view, e.g. side-wall retractors. The use of a second instrument may require the practitioner to operate both instruments at once simply to obtain a clear field of view. Alternatively, the practitioners may have to insert and adjust the speculum, setting its width with a clamping means, then insert and adjust the retractors before continuing with the medical procedure.

The use of multiple instruments can have several drawbacks. It is doubly intrusive into the patient's body and may cause more discomfort than the use of a single speculum alone. In many cases, it requires the practitioner to use both hands, which prolongs the procedure and impedes the physician's efficiency. In other cases, it will require the practitioner to set and maintain two instruments within the vaginal cavity. In either scenario, the use of multiple instruments may obstruct the practitioner's field of view of the vaginal interior. Thus, there is a particular need for a vaginal speculum that can be operated with one hand to retract the extraneous tissue which impedes the field of view through the vaginal canal or restricts the size of the vaginal cavity.

SUMMARY OF THE INVENTION

The present invention is directed towards a single instrument which has a handle and two pluralities of blades, is minimally intrusive into the patients body, and expands the vaginal cavity in both the vertical and horizontal axes, as well as towards a method of using the instrument to enlarge the vaginal opening/cavity to perform an examination or other medical procedure. The invention is a single instrument which removes from the field of view the extraneous tissue which pushes around the longitudinal blades. This feature enable the practitioner to efficiently and quickly perform a vaginal examination or procedure without undue manipulation of the speculum and without the use of an additional instrument. The vertical and horizontal axes as the terms are used herein are defined by the instruments orientation along the long axis of its handle.

In one preferred embodiment of the invention, the instrument includes a handle for the practitioner to manipulate and adjust the speculum, a longitudinal assembly including a plurality of adjustable, longitudinally arranged speculum blades which expand the vaginal cavity in a vertical direction, and a latitudinal assembly including a plurality of adjustable latitudinally arranged paddles or blades which expand the vaginal cavity in a horizontal direction, retracting the extraneous tissue from the practitioners field of view. The blades and paddles are contoured for the comfort of the patient and at least partially encompass a cavity forming an aperture along the practitioner's field of view.

In one embodiment of the invention, one of the longitudinal blades includes an inferior haft and an inferior blade, and one of the longitudinal blades includes a lever and superior blade. The lever is depressed or squeezed toward the haft by the practitioner following insertion of the speculum, which adjustably pivots the top and bottom longitudinal blades to expand the vaginal cavity. In one embodiment of the invention, the lever and handle are also linked by an adjuster device which is adjusted by the practitioner to keep the expansion of the top and bottom blades at a set width.

Each of the latitudinal or side wall members is moveably mounted to move in a horizontal direction. In one embodiment shown in FIGS. 1–4, these members are located interior to the longitudinal blades. Each of the side wall members include a sidewall paddle or blade which is inserted into the vaginal opening, and an arm for adjusting the side wall paddle. The members extend out of the vaginal opening, pivot upon the handle, and operably connect to an adjuster device. This adjuster device can be operated by the practitioner one-handed. This adjuster device expands and sets the side-wall or latitudinal paddles at the desired width for the practitioner. The latitudinal paddles are also contoured for the patient's comfort. Thus, in one embodiment, the speculum of the invention can be adjusted and manipulated one-handed by the practitioner.

In another aspect of the invention, a method of using the four-bladed seeculum is provided. The method includes the steps of inserting the speculum into the vaginal opening, expanding the longitudinal blades by depressing a lever and adjustably setting the width of these blades, expanding the latitudinal paddles within the vaginal canal to push aside the extraneous tissue which may impede the practitioners field of view, setting or expanding this set of blades one-handed, and proceeding with the medical procedure or examination as the practitioner sees fit. In one embodiment of the invention, adjustably setting the width of the blades may be performed one-handed.

DETAILED DESCRIPTION OF THE INVENTION

Figure 1:
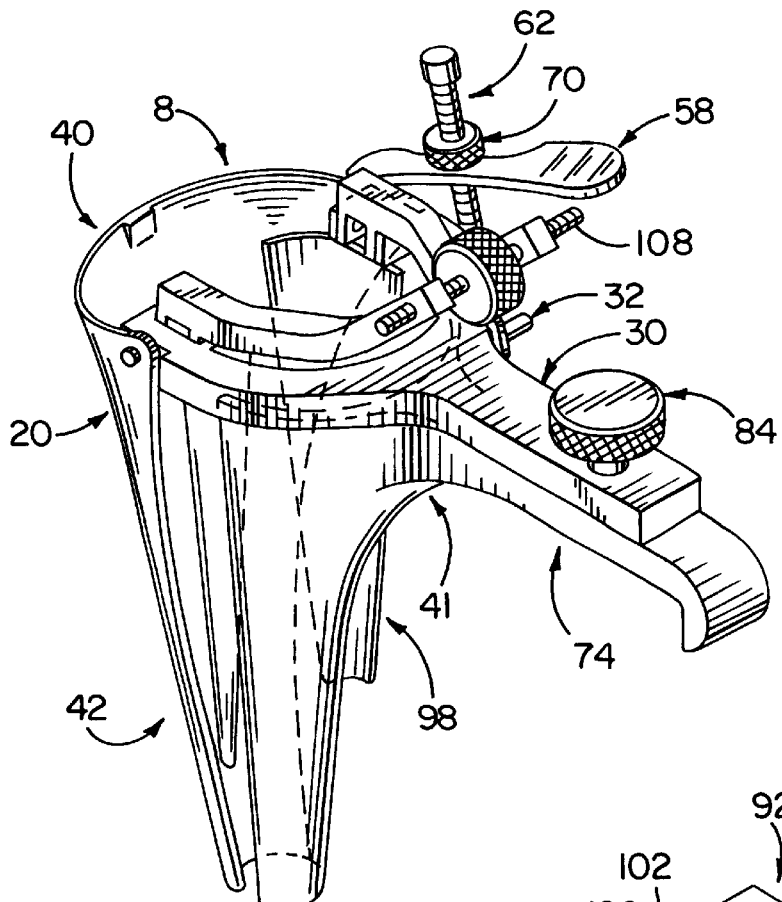
FIG. 1 depicts a perspective view of one embodiment of the assembled speculum of the invention.

The present invention relates to a vaginal speculum 20 for use during obstetrical/gynecological examinations and procedures. FIGS. 1–4, generally depict: a handle 30; a longitudinal assembly including a superior blade 40 and an inferior blade 41 for expanding the vaginal cavity in a vertical direction; and a latitudinal assembly 90 for expanding the vaginal cavity in the horizontal direction. As can be best seen in FIG. 2, the four main component parts of the speculum are arranged as follows: the superior blade 40 is mounted to the handle 30; the haft 74 of inferior blade 41 is mounted to the handle 30; and the latitudinal assembly 90 is mounted to the handle 30.

The speculum 20 is preferably made from stainless steel or an autoclavable plastic resin so that the speculum can be reused after being sterilized. However, it is also contemplated that the invention can be made from the standard materials used for disposable surgical devices. For example, the parts can be formed from a rigid plastic material such as polystyrene, ABS, or PVC.

Herein, the term proximate is defined as being toward the practitioner, the term distal as the being towards the patient, the longitudinal vertical axis is defined as the direction along the long axis of the proximate surface of the shaft 31 of the Y shaped handle 30, and the latitudinal or horizontal axis is defined as the direction along the short axis of the proximate surface of the shaft 31 of the Y shaped handle 30.

The longitudinal assembly, as depicted in this embodiment, includes a pair of speculum blades 40, 41 in a "Graves" configuration, which is named for the physician who originally designed the configuration. The Graves configuration includes a superior and inferior blade, both of which are rounded for the patient's comfort. However, it is contemplated that other speculum blade configurations which do not substantially interfere with the latitudinal blades motion may also be used.

Figure 2:
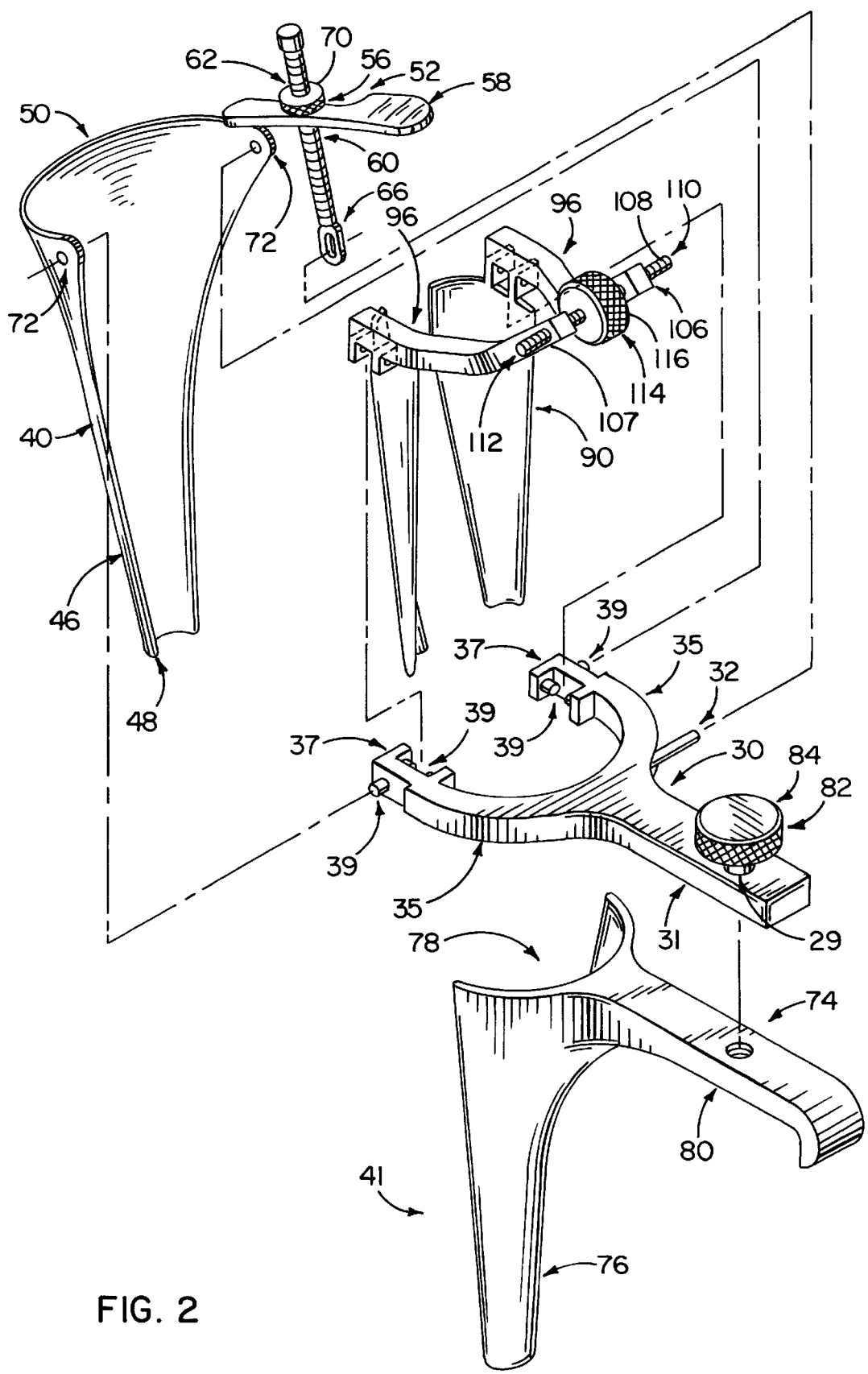
FIG. 2 depicts an exploded view of the speculum of FIG. 1.
Figure 4:
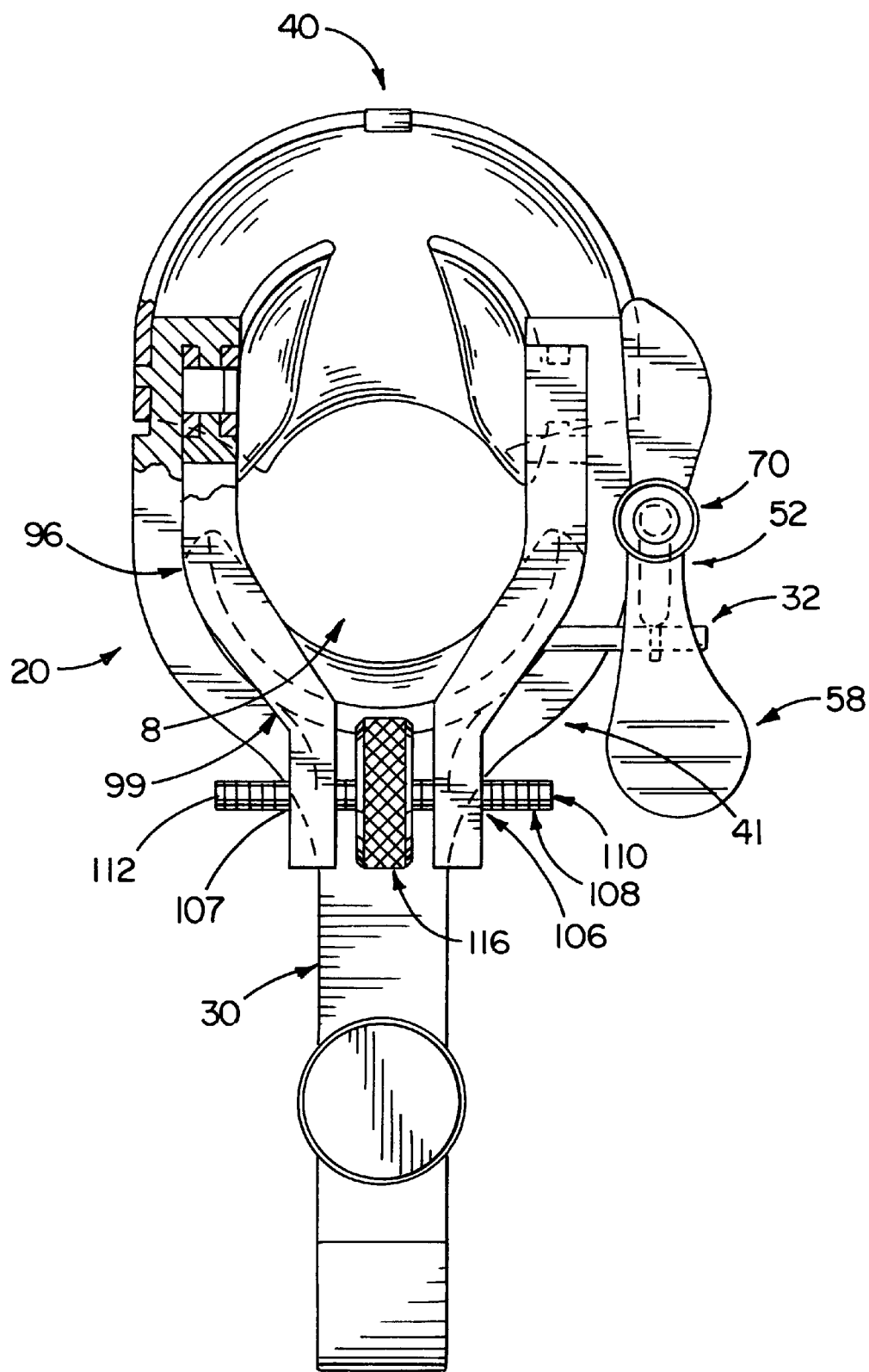
FIG. 4 depicts the physician's view through the viewing aperture of the speculum of FIG. 1.

The longitudinal assembly as depicted in FIG. 2 includes a superior blade 40 (FIG. 2) for expanding the vaginal cavity in an upward direction, and an inferior blade 41 (FIG. 2) for expanding the vaginal cavity in a downward direction. The superior blade 40 includes a superior blade portion 46 which, for purposes of this description, has a distal 48 and a proximal end 50, and a lever portion 52. Along the length of the superior blade between the distal 48 and proximate ends 50, the superior blade 40 is concave in shape, and the superior blade 40 is rounded at its distal end 48 for the patient's comfort. When in use, the blade is inserted into the vaginal opening, distal end 48 first. The lever 52, is joined to the superior blade 40 to form an interior angle between the lever and the superior blade which places the lever 52 within reach of an average practitioner's thumb in the speculum's full range of useable settings, from fully opened and fully closed. As best seen in FIG. 2 and FIG. 4, the lever 52 is joined to the superior blade 42, off-set from the viewing aperture 8. The superior lever 52 has a hole 56 about midway towards the proximate end, and is contoured and rounded to form an oblong surface 58, which the practitioner depresses to actuate the lever and cause the superior blade 40 to pivot relative to the inferior blade 41.

As shown in FIG. 1, passing through the hole 56 in the lever 52 is first adjustment pin 60. The first adjustment pin 60 has a threaded end 62 and a distal end. The distal end defines an eye-hole 66, an oblong shaped hole, which mounts upon a lateral pin 32. This lateral pin protrudes outwardly from the base of the arms of the Y-shaped handle 30. It is also contemplated that other pin mounting structures and mechanisms may be used to provide a mount for the first adjustment pin. For example, but without limitation, a bolt, screw or axle could be used to hold and mount the first adjustment pin in place. The threaded end 62 of the first adjustment pin 60 extends upwardly from the handle member 30 and, when mounted, passes through the hole 56 in the lever 52. This pin 60 is retained by a threaded retaining bolt 70. The threaded retaining bolt 70 is placed so that it can be adjusted by the practitioner while the speculum is being used one-handed to fix the width of the speculum blades.

While one-handed operation may be preferred by the practitioner for certain procedures, particularly where simultaneous manipulation of another instrument is required, it is contemplated that the speculum of the invention may be operated and adjusted using both hands when necessary.

As shown if FIG. 2, between the lever 52 and the distal end 48 of the superior blade 46 are two mounting apertures 72 which are on opposite sides of the arc formed by the concave surface of the superior blade 46. These mounting apertures 72 correspond to the first set of pivot points 39 of the handle 30. It is recognized that these mounting apertures 72 can be fully encompassed holes through the speculum, or partially encompassed arcs. The proximate end 50 of the superior blade 46 is shaped as an arc, which defines the upper part of the viewing aperture 8 seen in FIG. 4. It is recognized that one can also utilize planar or flat upper blades, in which case this viewing aperture 8 shown in FIG. 4 would have a planar or squared upper arc.

As shown in FIG. 2, the handle 30 is generally Y-shaped, and has two arms 35 projecting upwards from a shaft 31 to encompass the lower half of the viewing aperture 8 (FIG. 4). At the upper end of each of the arms 35 of the Y-shaped handle 30 are two sets of pivot points 35, 39, depicted here as short pins. The first set of pivots 39 are two pins which face outward from each other from the exterior of the upper end of the Y-shaped handle member arms 35. The first set of pivot points 39 are placed for mounting the superior blade 42 of the longitudinal assembly as discussed below. The second set of pivot points 39 is four pivot points, or pins, two on each arm of the Y-shaped handle 30. Two pins each extend towards each other upon upper and lower brackets 37 which project from the interior of the handle member arms 35, and this second set of pivot points 39 is used to mount the latitudinal assembly 90 shown in FIG. 3 and discussed below.

Also, the shaft 31 of the handle 30 is mounted to the second half of the longitudinal assembly, the inferior blade 44. The inferior blade 41 has a distal blade 76, proximate end 78, and depending haft 74. The distal end of inferior blade 76 is rounded for the patient's comfort and is also depicted in the "Graves" configuration, corresponding with the superior blade 46. The distal blade 76 is concave along its length and partially encloses a space with the superior blade 46. This space extends along the axis of the practitioner's line of sight through the viewing aperture 8 as shown in FIG. 4. The proximate end 78 of the inferior blade is concave or arc shaped. Depending on the placement of the Y-shaped handle, this arc or Y-shape may also define the lower portion of the viewing aperture 8. The haft 74 depends from the proximate end 78 of the inferior blade 44. In the embodiment depicted in FIG. 2, the haft 74 is formed of one piece with the distal blade 76, but it is recognized that these parts could be formed separately and joined or attached by any number of means, such as adhesives, or interlocking parts.

As shown in FIG. 2, about midway along the haft 74 of the inferior blade 41, there is a first mounting hole 80, which is threaded to receive a mounting bolt 82. The mounting bolt 82 has a threaded end, and a round bolt head 84. The shaft 31 of the handle 30 also has a threaded mounting hole, the second mounting hole 29, which corresponds with the first mounting hole 80 of the haft 74 of the inferior blade 41. The threaded end of the mounting bolt 82 passes through and engages the threads of the second mounting hole 29 in the handle 30, then passes through and engages the threads of the first mounting hole 80 of the haft 74. The round bolthead 84 can be turned manually so that the mounting bolt tightens and firmly joins the Y shaped handle 30 to the haft 74 of the inferior blade 41. Also, in the embodiment depicted, the haft 74 and Y-shaped handle 30 are shown as two separate parts. However, it is contemplated, the haft 74 and handle 30 may be adhered to one another or formed from a single piece of material, in which case, the handle and its associated structure would be integral with the inferior blade.

Figure 3:
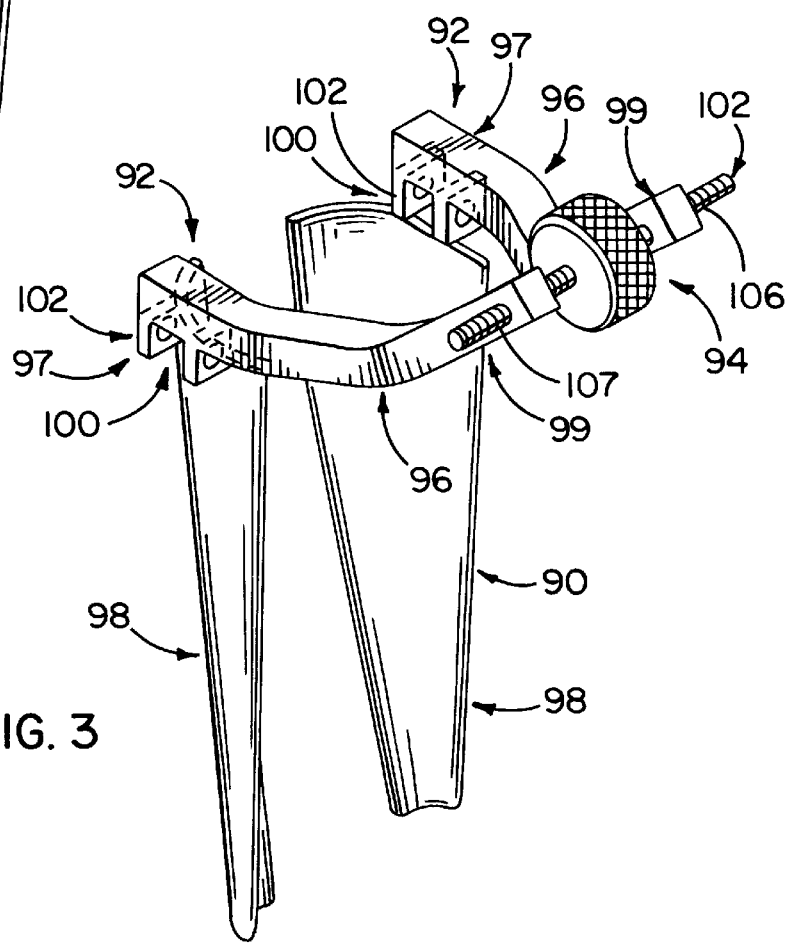
FIG. 3 depicts the latitudinal assembly of the speculum of FIG. 1.

FIG. 3 depicts the latitudinal assembly 90. As depicted, the latitudinal assembly 90 includes two corresponding sidewall members 92, and the two sidewall members are joined by a second adjuster device 94. Each sidewall member 92 has a proximate sidewall arm 96 and distal sidewall paddle or blade 98. The distal sidewall paddle 98 is rounded and blade shaped, and rests in the interior of the space enclosed by the concave shaped space partially enclosed by the longitudinal assembly. At its proximate end, each sidewall paddle extends to the viewing aperture 8 (FIG. 4) and is joined to the sidewall arm 96.

As can be seen in FIG. 3, the individual sidewall arms 96 and paddles 98 of the two sidewall members 92 are formed of one piece. It is contemplated that separately formed parts can also be used. The sidewall arm 96 has an upper 97 and a lower 99 portion. The upper portion 99 is joined to the sidewall paddle 98 and extends outward from the paddle 98 to form a U-shaped mounting bracket 100. This mounting bracket 100 has upper and lower holes 102 which correspond to and fit over the second set of pivot points 33 on the interior surface of the arms 35 of the Y-shaped handle 30. This arrangement of pivot points 33 and brackets 100 enables the sidewall paddles to expand in a latitudinal direction. It is contemplated that other mechanisms may be used to provide a moveable mount for the paddles. For example, but without limitation, a hinge and pin, a single pivot point, a single hole and single pin bracket or a ball joint could also be utilized for this purpose.

The lower portion 99 of the sidewall arm 96 is contoured to form an arc roughly equal in size and shape to the arc formed by the arms 35 of the Y-shaped handle 30, so as not to intrude into the viewing aperture 8. The proximate ends of the lower portions of the sidewall arms 96, are joined together by a second adjuster device 94. This device is used to adjust and set the distance between the sidewall arms by pivoting the sidewall blades towards and away from each other. As best seen in FIG. 4, each sidewall arm 96 has a threaded aperture at the proximate end of its lower portion 99. For convenience in this description, these threaded apertures are defined as the first 106 and second aperture 107. The first aperture 106 is threaded to correspond to a second adjustment pin 108. This second adjustment pin 108 has a first end 110 and second end 112 and a middle portion 114. The first end 110 is threaded to correspond to the first aperture 106 and is threaded through the aperture of the sidewall arm 96. The second end 112 is reversibly threaded with respect to the first end 110, and is threaded through the second aperture 107 to correspond with the other sidewall arm 96. Thus the apertures on the two sidewall arms are reversibly threaded with respect to each other. The middle portion of the pin 114 has a fixed thumb wheel 116 with a high friction circumference. It is contemplated that there are a number of adjusting devices which can be utilized to adjust the distance between the paddles. For example, and without limitation: a rachet and wheel; a ratch and pawl; a cam and pin; an adjustable hinge; or a spring could also be utilized for this purpose.

Figure 5:
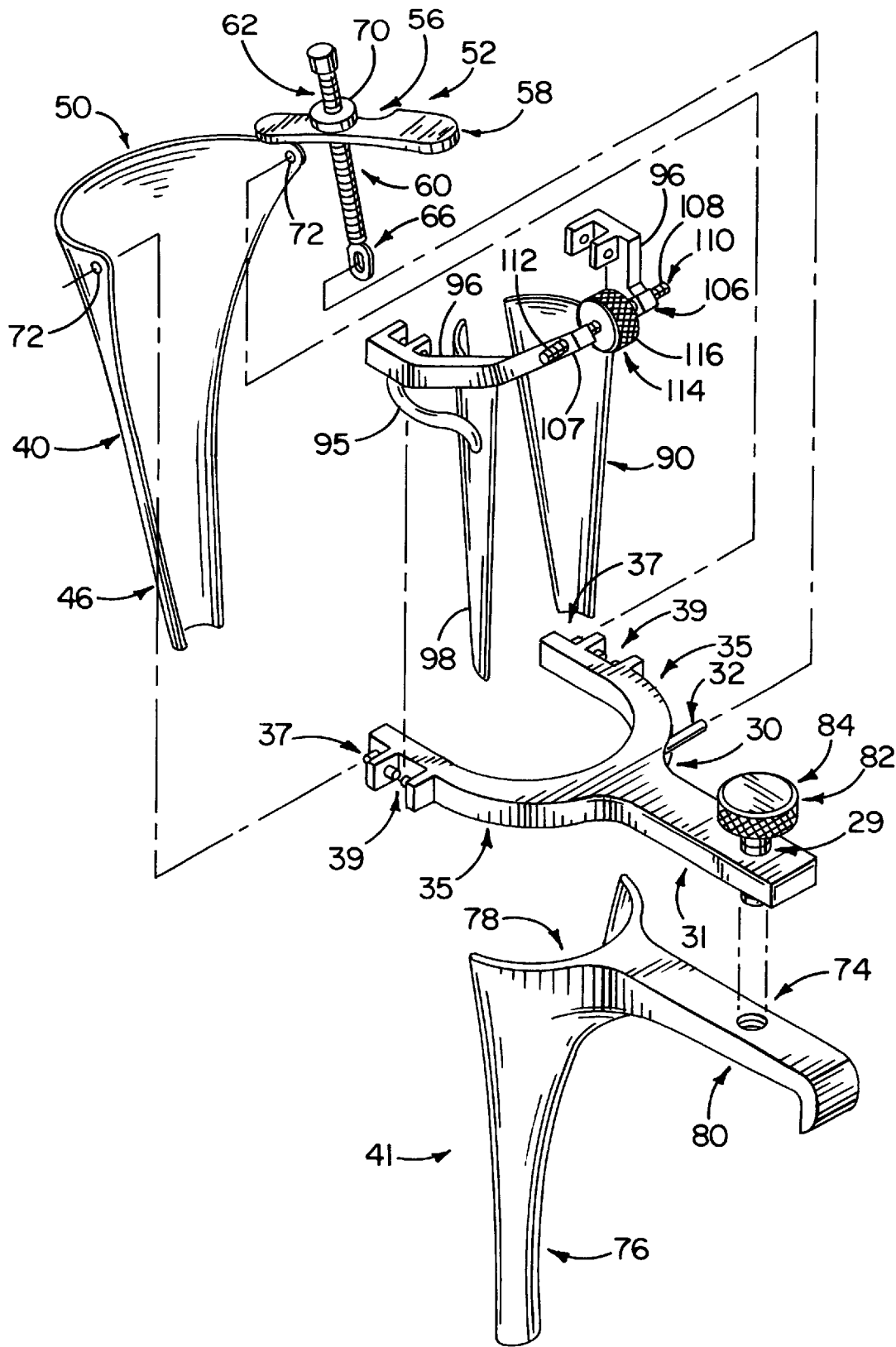
FIG. 5 depicts an exploded view of an additional embodiment of the speculum of the invention.

FIG. 5 depicts an additional embodiment of the invention, one which has the upper and lower brackets 37 projecting outward from arms 35 of the Y-shaped handle 30. Also, in this embodiment the latitudinal assembly 90 has a pair of extensions 95 which join the sidewall paddles 98 to the sidewall arms 96. These extensions 95 curve around the outside of arms 35 of the Y-shaped handle 30 to affix to the sidewall paddles 98. The extensions 95 as depicted in FIG. 5 are drawn elongated for emphasis and clarity in the drawing.

To operate the speculum shown in FIGS. 1–5, the practitioner gently inserts the longitudinal and latitudinal blades into the patient's vaginal opening. When the lever 52 on the superior blade 42 is depressed, the superior blade 46 is pivoted upwards, expanding the vaginal cavity by displacing vaginal tissue (not shown). Pressure from the displaced tissue provides counter-force on the superior blade 40, and the threaded retaining bolt 70 is turned by the practitioner to retain the lever 52 and keep the longitudinal assembly expanded at the width desired. When the thumbwheel 114 on the latitudinal assembly 90 is rotated, the sidewall paddles 98 pivot outwards from each other, retracting tissue which may impede into the viewing aperture 8 around the longitudinal blades. In use, the practitioner rotates the thumb wheel 114 to cause the adjuster to contract the sidewall arms 96 towards each other, which causes the sidewall paddles 98 to move away from each other, thus retracting the vaginal tissue which may protrude around the inferior and superior longitudinal blades.

It is recognized that changes or modifications may be made to the embodiments depicted and described herein without departing from the scope of the invention. Therefore, it is intended that the foregoing drawings and description shall be interpreted as an illustration of the invention and not as limitations upon the invention.

What is claimed:

1. A vaginal speculum for performing obstetrical and gynecological examinations and procedures, comprising:
   a handle for manipulating the speculum,
   a plurality of adjustable longitudinal blades for expanding the vaginal cavity in a vertical direction, said longitudinal blades being mounted on said handle and being arranged to create an unobstructed viewing aperture for inspecting the interior of the vaginal cavity while the handle is manipulated by a practitioner; and
   a plurality of adjustable latitudinal blades for expanding the vaginal cavity in a horizontal direction, said latitudinal blades being mounted on said handle and being arranged to create an unobstructed viewing aperture for inspecting the interior of the vaginal cavity while the handle is manipulated by a practitioner.

2. The vaginal speculum of claim 1, further comprising an adjuster for adjusting a distance between at least two of the plurality of adjustable latitudinal blades, said adjuster operably fixed to and joining the at least two of the plurality of adjustable latitudinal blades.

3. The vaginal speculum of claim 2, wherein said adjuster includes a reversibly threaded pin, and a thumbwheel axially fixed to said reversibly threaded pin, said plurality of moveably mounted latitudinal blades each having a reversibly threaded aperture, said reversibly threaded apertures corresponding to and operably engaging said reversibly threaded pin.

4. The vaginal speculum of claim 1, wherein said plurality of latitudinal blades includes a first latitudinal blade and a second latitudinal blade, a first arm joined to said first latitudinal blade, a second arm joined to said second latitudinal blade, and wherein the vaginal speculum further includes an adjuster for setting the distance between said first and said second arms, said adjuster including a reversibly threaded pin, and a thumbwheel axially fixed to said reversibly threaded pin, said first and said arms each having a reversibly threaded aperture, and said apertures corresponding to and operably engaging said reversibly threaded pin.

5. A vaginal speculum comprising:
   a handle for manipulating the vaginal speculum;
   a longitudinal assembly for expanding the vaginal cavity along the longitudinal axis, said longitudinal assembly including
      a superior blade for expanding the vaginal cavity in an upward direction, said superior blade including a superior lever, a superior speculum blade joined to said superior lever, and a first adjuster integrally joined to said superior lever portion,
      an inferior blade for expanding the vaginal cavity in a downward direction, said inferior blade including, an inferior haft for mounting the inferior blade to the handle, said inferior haft affixed to said handle, and an inferior speculum blade joined to said inferior haft;
      wherein said superior blade is pivotally and adjustably mounted upon said handle;
   a latitudinal assembly for expanding the vaginal cavity along the latitudinal axis of the patient's pelvic region, said latitudinal assembly moveably mounted to said handle, said latitudinal assembly including
      a first side-wall paddle for expanding the vaginal cavity in a first latitudinal direction, said first side wall paddle pivotally and adjustably mounted on said handle, and
      a second side-wall paddle for expanding the vaginal cavity in a second latitudinal direction, said second side wall paddle pivotally and adjustably mounted on said handle.

6. The vaginal speculum of claim 5, wherein said haft and said handle are formed as a single piece.

7. The vaginal speculum of claim 5, further comprising an adjuster for setting the width vaginal opening made by the first and second side wall paddles, said adjuster operably mounted to said first and second side wall paddles.

8. The vaginal speculum of claim 7, wherein said adjuster further comprises a reversibly threaded pin, said reversibly threaded pin including a first end, said first end adjustably threaded through the side wall paddle, and a second end, said second end adjustably threaded through to the second side wall paddle.

9. The vaginal speculum of claim 5, wherein said first side wall paddle further comprises a first blade portion for insertion into the vaginal cavity, a first arm potion for manipulating the first blade portion, said first arm portion joined to said first blade portion, wherein said second side wall paddle further comprises, a second blade portion for insertion into the vaginal cavity, a second arm portion for manipulating the second blade portion, said second arm portion joined to said second blade portion, and an adjuster for setting the width of the vaginal opening, said adjuster operably linked to said first arm portion end said second arm portion.

10. The vaginal speculum of claim 9, wherein said adjuster further comprises:
   an adjustment pin for linking said first and second arm portions, said adjustment pin having a first and a second threaded end, said first and second ends reversibly threaded with respect to each other,
   said first arm further including a first threaded aperture, said first threaded aperture located distal to said first blade,
   said second arm including a second threaded aperture, said second threaded aperture located distal to said second blade, wherein said first and second threaded apertures are reversibly threaded with respect to each other, and said first end operably corresponds to said first aperture and said second end operably corresponds to said second aperture.

11. The vaginal speculum of claim 10, further comprising a thumbwheel for turning the adjustment pin, said thumbwheel mounted on the axis of the adjustment pin.

12. A vaginal speculum, comprising:
   a Y-shaped handle for manipulating the speculum, said Y-shaped handle including a set of arms and a shaft depending from said set of arms,
      said set of arms extending upwards from the shaft to form the viewing aperture, said set of arms including a plurality of interior pivot points, said plurality of interior pivot points located on the interior surface of the set of arms, and a plurality of exterior pivot points, said plurality of exterior pivot points located on the exterior surface of the set of arms,
   an inferior assembly for expanding the vaginal cavity, said inferior assembly including an inferior speculum blade for insertion into the vaginal cavity, an inferior haft for mounting the inferior speculum blade, said inferior haft affixed to said handle, and said inferior haft joined to the inferior speculum blade to form an approximate L-shape;
   a superior assembly for expanding the vaginal cavity, said superior assembly including a superior speculum blade for insertion into the vaginal cavity, a superior lever for adjusting said superior speculum blade, said superior lever joined to the superior speculum blade to form an approximate L-shape,
   a first adjuster for pivotally separating and adjusting said superior and inferior speculum blades, said first adjuster operably linked to the superior lever and Y-shaped handle,
   a plurality of side wall members for retracting the patients tissue intruding from the sides of the vaginal cavity, said plurality of side wall members including at least a first and second side, wall member, said first side wall member including a first paddle for insertion into the vaginal cavity, and a first arm for adjusting the first paddle, said first arm joined to the proximate end of the first paddle, said second side wall member including a second paddle for insertion of into the vaginal cavity, and a second arm for adjusting the second paddle, said second arm joined to the proximate end of the second paddle,
   a second adjuster for pivotally separating said plurality of side wall blades, said second adjuster operably linked to the first and second side wall arms, wherein the plurality of side wall members are pivotally and adjustably mounted upon the interior plurality of pivot points, and said superior member is pivotally and adjustably mounted to said exterior plurality of pivot points.

13. The vaginal speculum of claim 12, further comprising a threaded aperture for mounting the second adjuster, said threaded aperture located on the first sidewall blade arm distal from said first sidewall blade, a reverse threaded aperture for mounting the adjuster, said reverse threaded aperture located on the second sidewall blade handle distal from the second side wall blade, said second adjuster including an adjustment pin for adjustably connecting the first and second set of sidewall blade handles, said adjustment pin having a threaded end and a reverse-threaded end, said threaded end operably threaded through the threaded aperture, said reverse threaded end operably threaded through the second aperture.

14. The vaginal speculum of claim 12, further comprising an interior speculum cavity, said cavity enclosed by the superior and inferior blade portions, wherein the first and second side wall paddles are enclosed within said interior speculum cavity.

15. The vaginal speculum of claim 12, wherein said second adjuster includes at least one rachet for adjusting the distance between the arms, said rachet for releasably engaging the sidewall arms, said rachet including a first end and a second end, said first end mounted on the first side wall arm and said second end extending towards the second side wall arm.

16. The vaginal speculum of claim 13, said adjustment pin further comprising a thumbwheel for turning said pin, said thumbwheel fixedly mounted upon the pin along the pin's central axis.

17. A method of using a vaginal speculum for a gynecological or obstetrical procedure, comprising:

inserting the speculum into the vaginal cavity, said speculum including a plurality of movably mounted adjustable longitudinal blades and a plurality of movably mounted adjustable latitudinal paddles;

manipulating a handle on the speculum while maintaining an unobstructed viewing aperture for inspecting the interior of the vaginal cavity;

opening said longitudinal blades to vertically expand the vaginal cavity;

adjusting to set the distance between said longitudinal blades;

opening said latitudinal paddles to horizontally expand the vaginal cavity; and adjusting to set the distance between said latitudinal paddles.

18. The method of claim 17, wherein the diameter of the viewing aperture remains substantially constant during the usage of the speculum.

19. The method of claim 17, wherein the steps of opening and adjusting said longitudinal blades to set the distance between said longitudinal blades, and the steps of opening and adjusting said latitudinal blades to set the distance between said latitudinal blades, are performed by the practitioner with the same hand which holds the speculum.

* * * * *